United States Patent [19]

Shimazaki et al.

[11] Patent Number: 5,739,171
[45] Date of Patent: Apr. 14, 1998

[54] METHOD FOR PROMOTING ANIMAL GROWTH

[75] Inventors: Gisen Shimazaki, Osaka; Chen Jian Jun, Kobe; Norio Ohara, Nara-ken, all of Japan

[73] Assignee: Asahi Chemical Manufacturing Co., Ltd., Osaka, Japan

[21] Appl. No.: 797,737

[22] Filed: Feb. 11, 1997

Related U.S. Application Data

[63] Continuation of Ser. No. 436,956, May 8, 1995, abandoned, which is a continuation-in-part of Ser. No. 227,460, Apr. 14, 1994, abandoned.

[30] Foreign Application Priority Data

Apr. 21, 1993 [JP] Japan ................... 5-119045

[51] Int. Cl.$^6$ .................... A61K 31/075; A61K 31/045
[52] U.S. Cl. ................................ 514/716; 514/728
[58] Field of Search ........................... 514/716, 728

[56] References Cited

U.S. PATENT DOCUMENTS 3,199,971 8/1965 Shimazaki .
4,045,554 8/1977 Springer ........................ 424/164
4,935,450 6/1990 Cone, Jr. ........................ 514/728

FOREIGN PATENT DOCUMENTS 42-20399 10/1967 Japan .
2-131468 A 5/1990 Japan .

OTHER PUBLICATIONS

BIOSIS Abstract 10486420, Biosis No.: 96086420 (Pahm et al.), 1993.

Chemical Abstracts 72:2441e (1970), Shimazaki.

"The Merck Index" (11th Ed.), Budavari et al., Merck and Co., Inc., Rahway, NJ., 1989, p. 1047.

Primary Examiner—Marianne M. Cintins
Assistant Examiner—M. Moezie
Attorney, Agent, or Firm—Armstrong, Westerman, Hattori, McLeland & Naughton

[57] ABSTRACT

Methods for promoting animal growth comprising administering one or more substances selected from o-nitrophenol, p-nitrophenol, 5-nitroguaiacol and salts thereof as active ingredients.

14 Claims, No Drawings

METHOD FOR PROMOTING ANIMAL GROWTH

This application is a continuation of application Ser. No. 08/436,956 filed May 8, 1995, now abandoned, which is a continuation-in-part of application Ser. No. 08/227,460 filed Apr. 14, 1994 now abandoned.

This invention relates to a method for promoting the growth of animals.

PRIOR ART

Various pharmaceuticals and other substances such as vitamins, hormones, microelements and others have been used for promoting the growth and vitality of animals. In general, hormones dosage should be strictly adjusted to the genus, sex and age of the animal. Thus the application method of hormones is difficult. In addition hormones are expensive and have adverse effect on the consumers of the products from hormone treated animals.

Polypeptides which exhibit a growth promoting activity have been isolated from pituitary glands of vertebrates and also from chickens and their chemical structures have been determined. On the other hand, however, such growth promoting substances of polypeptide type are expensive and, when they are administered orally, they are decomposed by proteinases in stomach and intestine whereby their effect decreases. Accordingly; the method of administration is to be intramuscular or intravenous injection and their mode of use is restricted.

Even in the case of fishes, polypeptides exhibiting a growth promoting activity have been isolated from pituitary glands and their chemical structures and genes for their synthesis, have been determined. There are known methods for production of these peptides by microorganisms. However, their application is limited as they are highly specific and are effective only on the particular fish genus from which the genetic material has been derived.

Even though vitamins and microelements have been broadly used in animal feeds, their objective is to supply proper amounts of those elements to avoid disorders caused by their difficiency including the growth retardation, and increasing levels of their administration above the required levels is not effective and does not increase growth above the typical average values.

Further, pharmaceuticals with various actions have been proposed for animal growth promotion. However, in many cases there were safety problems and their effect was different on different genus of animals, and actually their effect was not satisfactory for a wide range of farm animals, pets, birds, fishes etc.

PROBLEMS TO BE SOLVED BY THE INVENTION

The present invention has been achieved by solving the above-mentioned problems and the objective of the present invention is to offer an animal growth promoting composition and method therefor that is easy to apply, safe and effective on a wide range of animals including farm animals, pets, birds, fish, shrimp, crab and other aquacultures.

MEANS TO SOLVE THE PROBLEMS

The present inventors have carried out extensive studies for solving the above-mentioned problems and found that the objective can be achieved by the method comprising administering a therapeutically effective amount of; one or more substance(s) selected from o-nitrophenol, p-nitrophenol, 5-nitroguaiacol and salts thereof.

Thus, the present invention relates to an animal growth promoting composition and method therefor comprising administering an effective amount of; one or more substance(s) selected from o-nitrophenol, p-nitrophenol, 5-nitroguaiacol and salts thereof as active ingredient(s).

o-nitrophenol, p-nitrophenol and 5-nitroguaiacol which are used in the present invention have structures expressed by the following formulae and, in the present invention, they may be used in a free or salt form.

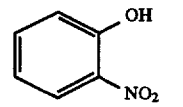

o-Nitrophenol

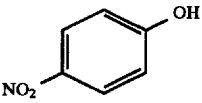

p-Nitrophenol

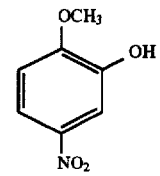

5-Nitroguaiacol

Incidentally, sodium o-nitrophenol, sodium p-nitrophenol and sodium 5-nitroguaiacol are active ingredient(s) for ATONIK (manufactured by Asahi Chemical MFG. Co., LTD.) which is a product stimulating germination, root formation and growth of plants and is a known plant growth regulator (cf. Japanese Patent No. 470,256). Moreover, sodium 5-nitroguaiacol has been used as a hair growth promoter (cf. Japanese Patent 526,345) and, in the past, it was used in a form of injection with a trade name of Chloromatin (manufactured by Nikko Pharmaceutical Co., LTD.) as an analgesic, antiinflammatory, antitussive for, stimulation of appetite and for the prevention of intestinal infection.

However, there has been neither example for the use of those compounds for growth promotion of animals nor any report that they exhibit a growth promoting activity.

o-Nitrophenol, p-nitrophenol, 5-nitroguaiacol and salts thereof which are active ingredient(s) of the growth promoting composition for animals according to the present invention are commercially sold in market as chemical reagents and are easily available but they may also be synthesized by the following methods.

For example, o-nitrophenol may be synthesized by nitration of phenol with nitric acid followed by subjecting the resulting nitrated compound to a steam distillation while p-nitrophenol may be prepared by isolating a precipitate in the residue after the above steam distillation followed by recrystallization, which is one of the common purifying means.

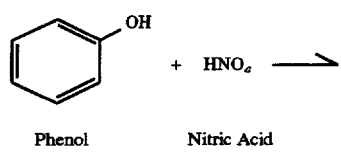

Phenol + HNO₃ →

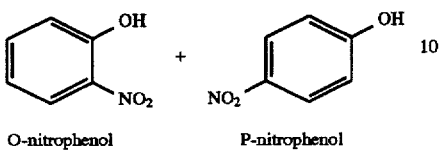

O-nitrophenol + P-nitrophenol

5-Nitroguaiacol may be prepared, for example, as follows. Thus, as shown below, guaiacol is used as a starting material, acetylated with acetic anhydride, nitrated with nitric acid, saponified with an alkali such as sodium hydroxide, neutralized with hydrochloric acid or the like and then the precipitate is separated.

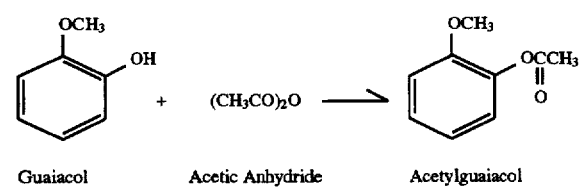

Guaiacol + Acetic Anhydride → Acetylguaiacol

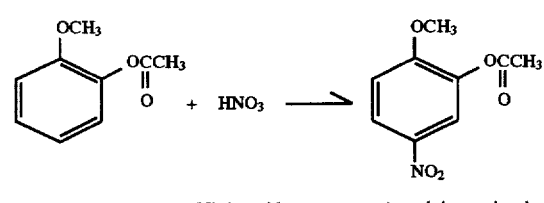

+ HNO₃ → Acetylnitroguaiacol

Nitric Acid

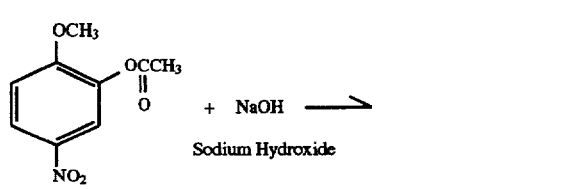

+ NaOH →

Sodium Hydroxide

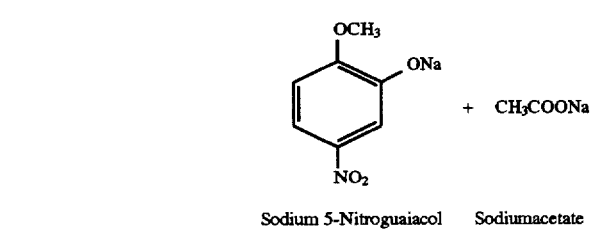

Sodium 5-Nitroguaiacol + Sodiumacetate

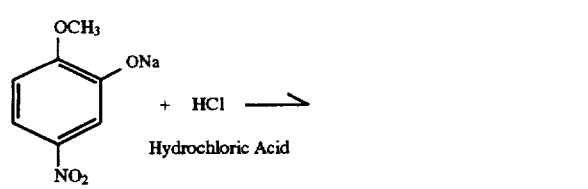

+ HCl →

Hydrochloric Acid

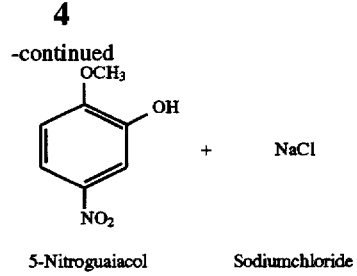

5-Nitroguaiacol + NaCl

Sodiumchloride

Salts of o-nitrophenol, p-nitrophenol and 5-nitroguaiacol may be prepared by common neutralizing methods though there is no limitation as to the method whereby salts are prepared by neutralization. Alkali is usually used as the neutralizing agent therefor and preferred alkali used for the neutralization are common alkali and alkali earth metal hydroxides, ammonia, alkylamines and organic amines such as ethanolamine etc.

Safety of the effective components of the composition of the present invention will be given hereunder. For example, acute toxicity by oral administration of sodium o-nitrophenol, sodium p-nitrophenol and sodium 5-nitroguaiacol is as follows:

Sodium o-nitrophenol. $LD_{50}$ for rats(male): 2050 mg/kg, (female): 1460 mg/kg;

Sodium p-nitrophenol. $LD_{50}$ for rats(male): 1250 mg/kg, (female) 482 mg/kg;

Sodium 5-nitroguaiacol. $LD_{50}$ for rats (male): 3100 mg/kg, (female): 1270 mg/kg.

Acute toxicity by oral administration is low. In addition, it has been also confirmed that those compounds are without problem in terms of toxicity by chronic toxicity test, teratogenic test and carcinogenic test. Further, as mentioned above, those compounds have been used as plant growth regulators and hair growth promoters throughout the world. In the past, they were used as injections but there was no example of adverse affection on the animals who took the plants to which they were applied, on the persons who were injected therewith and on the persons using the hair growth promoters containing them. Thus, their safety in humans has been practically confirmed. As mentioned above, o-nitrophenol, p-nitrophenol, 5-nitroguaiacol and salts thereof which are active ingredient(s) of the methods for growth promoting of the present invention have high safety.

It is sufficient that the methods for promoting growth in animals in accordance with the present invention comprises administering one or more compounds selected from o-nitrophenol, p-nitrophenol, 5-nitroguaiacol and salts thereof as active ingredient(s). For example, one of o-nitrophenol, p-nitrophenol, 5-nitroguaiacol and salts thereof or a mixture of two or more substances thereof may be used. Further, a mixture of one or more substance(s) selected from those active ingredient(s) with a liquid or solid carrier may be used as well. Further, feed containing one or more of those active ingredient(s) may be used too.

The methods of growth promoting in animals in accordance with the present invention may be administered in a form of liquid, paste, powder, granules, tablets, pellets, large pills, etc.

Examples of the applicable carrier are liquid such as water, ethyl alcohol, plant oil, etc.; mineral products such as clay, kaolin, talc, diatomaceous earth, etc.; inorganic salts such as calcium carbonate, calcium phosphate, magnesium sulfate, etc.; sugars such as lactose, glucose, oligosaccharides, etc.; starch of potato, corn, wheat, barley, etc.; and wheat, barley, corn, sea algae, fish powder, meat powder, yeast, etc. in coarse powder used for feed.

With regard to feed, any of them for farm animals, pets, farm fish, etc. which are commercially available will do. Moreover, any feed which is prepared by mixing, in a suitable ratio, with cereals such as barley, wheat, milo, corn, etc.; root vegetables such as potato, sweet potato, etc.; leafy vegetables such as raddish leaves, white Dutch clover, etc.; straws of plant of rice, barley, etc.; chaffs and brans such as wheat bran, rice bran, etc.; by-products of processing of agricultural products such as soybean cake, molasses, soy sauce cake, starch pulp, corn meal, etc.; by-products upon processing livestock product such as meat powder, blood meal, etc.; and others such as sea algae, yeast, powder skim milk, bone powder, etc. will do.

Another aspect of the growth promoting composition for animals according the present invention is directed to methods for promoting growth in animals comprising administering a therapeutically effective amount of one or more compounds selected from o-nitrophenol, p-nitrophenol, 5-nitroguaiacol in combination with one or more; vitamins, amino acids, inorganic salts, microelements, and another additives or diluents etc.

Concentration of the active ingredient(s) administered is 0.00001% by weight or more and, preferably, from 0.0001 to 50% by weight.

Dose administered to animals in terms of active ingredient (s) is 0.01–100 mg/kg/day or, preferably, 0.1–10 mg/kg/day.

The methods of the present invention for promoting growth include administering the compounds to animals by various means. For example, the composition compounds per se may be given by oral administration or by hypodermic, intramuscular or intravenous injection; the compounds may be dissolved or suspended in drinking water; the compound may be mixed with feed; etc. For fishes, the compound may be dissolved or suspended in water of fish habitat or in a breeding water in addition to the above-mentioned methods.

The methods in accordance with the present invention exhibits a growth promoting effect to wide ranges of animals including farm animals and poultries such as pigs, cattles, horses, sheep, goats, dogs, cats, chickens, turkeys, ducks, geese, etc.; fishes such as carps, crucian carps, tilapias, catfish, ayu, sea breams, flatfish, yellowtails, etc.; and shell fishes such as shrimps, crabs, etc.

The present invention will be further illustrated by way of the following examples though the present invention is not limited to these examples.

EXAMPLE 1

Yorkshire piglets of two months age were fed with commercially available feed. A control group was fed with commercially available feed only while the group 1 was fed with the feed containing 0.75 mg/kg of sodium o-nitrophenol, 1.13 mg/kg of sodium p-nitrophenol and 0.38 mg/kg of sodium 5-nitroguaiacol and the group 2 was fed with the feed containing 1.50 mg/kg of sodium o-nitrophenol, 2.25 mg/kg of sodium p-nitrophenol and 0.75 mg/kg of sodium 5-nitroguaiacol. Each group comprised two male and female piglets (four in total) and their body weights were measured after feeding for ten weeks. The result is given in Table 1.

TABLE 1

| Group | Body Weight Increase per piglet |
| --- | --- |
| Control | 13,500 g (100) |
| Group 1 | 16,874 g (125) |
| Group 2 | 21,750 g (161) |

It is clear from the result of Table 1 that, in the groups to which the feed containing sodium o-nitrophenol, sodium p-nitrophenol and sodium 5-nitroguaiacol were added showed higher body weight increase than the control.

EXAMPLE 2

Broilers were fed with the commercially available feed for chickens in an amount of 5% to the body weight daily. The treated group was given with a drinking water containing 0.6 ppm of sodium o-nitrophenol, 0.9 ppm of sodium p-nitrophenol and 0.3 ppm of sodium 5-nitroguaiacol while the control group was given only with water. The way of administration was that, once (24 hours) a week, the water containing those compounds was given so that the animals can freely drink it while, on other days, only water was given the same as the control group. A group of 8 broilers formed one replication; there were 16 replications in each treatment. After breeding for seven weeks, their body weight and numbers of survived animals were determined and increases in body weight and feed conversion rate were calculated. The result is given in Table 2.

TABLE 2

| Group | Body Wt. Increase per Broiler | Survived Nos. | Feed Conversion Rate |
| --- | --- | --- | --- |
| Control Gr. | 1807 (100) | 123/128 | 1.979 |
| Treated Gr. | 2041 (113) | 125/128 | 1.851 |

It is clear from the result of Table 2 that, in the treated group to which a drinking water containing sodium o-nitrophenol, sodium p-nitrophenol and sodium 5-nitroguaiacol was given, the increase of body weight, survival and feed conversion rate were better than in the control group.

EXAMPLE 3

Tilapia fry with average body weight 2 g were used. Commercial feed for tilapia was given twice a day (morning and evening) in an amount of 5 to 8% of the body weight. The control group was given the commercial feed only, while the treated groups were given the commercial feed with the addition of the test compound(s) o-nitrophenol, p-nitrophenol and/or 5-nitroguaiacol, in the amount(s) shown in Table 3. Body weights were measured after 4 and 8 weeks. The results are given in Table 3.

TABLE 3

| Treatment Groups | | Body Weight Increase (g) per 1 Tilapia after | |
| --- | --- | --- | --- |
| | | 4 Weeks | 8 Weeks |
| Control | | 3.78 (100) | 10.10 (100) |
| Na o-nitrophenol | 10 ppm | 3.97 (105) | 10.71 (106) |
| Na p-nitrophenol | 10 ppm | 4.04 (107) | 10.61 (105) |

TABLE 3-continued

| Treatment Groups | | Body Weight Increase (g) per 1 Tilapia after | |
|---|---|---|---|
| | | 4 Weeks | 8 Weeks |
| Na 5-nitroguaiacol | 10 ppm | 4.08 (108) | 11.09 (110) |
| Na o-nitrophenol + Na p-nitrophenol | 5 ppm 5 ppm | 4.12 (109) | 10.80 (107) |
| Na o-nitrophenol + Na 5-nitroguaiacol | 5 ppm 5 ppm | 4.16 (110) | 11.18 (111) |
| Na p-nitrophenol + Na 5-nitroguaiacol | 5 ppm 5 ppm | 4.27 (113) | 10.80 (107) |
| Na o-nitrophenol + Na p-nitrophenol + Na 5-nitroguaiacol | 5 ppm 5 ppm 5 ppm | 4.35 (115) | 11.45 (113) |

It is clear from the result of Table 3 that, all of the groups to which the feed containing one or more substance(s) selected from sodium o-nitrophenol, sodium p-nitrophenol and sodium 5-nitroguaiacol was added, showed higher body weight increase than the control.

EXAMPLE 4

Grass carps of 1.8–2.1 cm length and 0.18 g of average body weight were used. With regard to the feed, that for breeding fish which is commercially available was used and given daily in an amount of 3–5% of the body weight. A 100 liter water tank for breeding fishes was used. Each group comprised 40 grass carps. Water in the tank was exchanged with a new one every day and the breeding was conducted. The control group was given only tap water while, in the treated group, tap water containing 0.03 ppm of sodium o-nitrophenol, 0.045 ppm of sodium p-nitrophenol and 0.015 ppm of sodium 5-nitroguaiacol was given one day in a week and, on other days, tap water without additives was given the same as in the control. Body weight was measured after 64 days. The result is given in Table 4.

TABLE 4

| Group | Body Weight Increase per Grass Carp | Survived Number |
|---|---|---|
| Control Gr. | 33.6 g (100) | 33/40 |
| Treated Gr. | 41.2 g (123) | 38/40 |

It is clear from the result of Table 4 that higher body weight increase of grass carps was noted when sodium o-nitrophenol, sodium p-nitrophenol and sodium 5-nitroguaiacol were added into water.

EXAMPLE 5

Fries of catfish (body weight: 130–140 g) were used. The feed as shown in Table 5 was given every day in an amount of 5 to 8% of the body weight. The control group was given only with this feed while the treated group was given with a feed to which 6 ppm of sodium o-nitrophenol, 9 ppm of sodium p-nitrophenol and 3 ppm of sodium 5-nitroguaiacol were added. Each replication comprised of twenty fries; there were 3 replications in each treatment. A 110 liter water tank was used and the cultivation was carried out for eight weeks in running water which was sterilized by heat and ultraviolet light. The body weight was measured. The result is given in Table 6.

TABLE 5

| Composition of the Feed for Catfish | |
|---|---|
| Name of the Material | Amount of the Material |
| Fish powder | 10.0% |
| Soybean | 48.5% |
| Corn | 30.0% |
| Cellulose | 1.0% |
| Soybean oil | 1.5% |
| Mixed vitamins | 3.0% |
| Mixed minerals | 4.0% |
| Binder | 2.0% |

TABLE 6

| Group | Body Weight Increase per Fry | Survied Numbers | Feed Conversion Rate |
|---|---|---|---|
| Control Gr. | 159.9 (100) | 58/60 | 1.838 |
| Treated Gr. | 192.5 (120) | 60/60 | 1.618 |

It is clear from the result of Table 6 that, in the treated group which was given with a feed containing sodium o-nitrophenol, sodium p-nitrophenol and sodium 5-nitroguaiacol, body weight increase, survival and feed conversion rate were better than in the control group.

EXAMPLE 6

Shanghai crabs of average body weight of 5.2 g were used. The feed was a mixture of 15% of fish meat, 15% of oyster meat, 10% of silkworm pupa and 60% of water plant and was given to the crabs every day in an amount of 20–30% of the body weight. In the control group, only said feed was given while, in the treated group, the feed containing 6 ppm of sodium o-nitrophenol, 9 ppm of sodium p-nitrophenol and 3 ppm of sodium 5-nitroguaiacol was given. The test was conducted in an area of 15 m$^2$ for one group which comprised 150 crabs. The body weight after 117 days was measured. The result is given in Table 7.

TABLE 7

| Group | Body Weight Increase per Crab |
|---|---|
| Control Group | 40.0 g (100) |
| Treated Group | 46.2 g (116) |

It is clear from the result in Table 7 that, in the treated group given the feed containing sodium o-nitrophenol, sodium p-nitrophenol and sodium 5-nitroguaiacol, higher increase of body weight was noted than in the control group.

EXAMPLE 7

The test was conducted on an area of 660 m$^2$ per group using 20,000 Taisho shrimps of average size of 3.4 cm. Commercially available feed for shrimps was used and given every day in an amount of 20% of the body weight. In the control group, only commercially available feed was given while, in the treated group, the feed containing 6 ppm of sodium o-nitrophenol, 9 ppm of sodium p-nitrophenol and 3 ppm of sodium 5-nitroguaiacol was given. The total weight of the shrimps was measured after cultivating for 75 days. The result is given in Table 8.

TABLE 8

| Group | Total Weight |
| --- | --- |
| Control Group | 86.75 kg (100) |
| Treated Group | 109.35 kg (126) |

It is clear from the result in Table 8 that, in the treated group to which a feed containing sodium o-nitrophenol sodium p-nitrophenol and sodium 5-nitroguaiacol was given, an increase of total weight was higher than in the control group.

As a result of the present invention a composition with high safety exhibiting excellent growth promoting effect to animals is offered. Said composition also achieves a growth promoting effect to wide varieties of animals including farm animals and pets, poultries, fishes, shell fishes, etc.

The methods of the present invention may be administered by various routes such as oral administration or by intramuscular or intravenous injection and by dissolving or suspending in the cultivating water. Sufficient growth promoting effect can be achieved by any of those administering methods.

As mentioned already, the active ingredient(s) of the methods of the present invention can be synthesized by relatively simple steps and, therefore, their production cost is low and, in addition, the raw materials used are inexpensive whereby the price of the active ingredient is low. Consequently, the lower cost and high efficacy of the methods of the present invention make them very cost effective.

What we claim is:

1. A method for promoting growth of an animal which comprises administering to the animal a growth promoting amount of one or more compounds selected from the group consisting of o-nitrophenol, p-nitrophenol and 5-nitroguaiacol, and salts thereof.

2. A method for promoting growth of an animal which comprises administering to the animal a growth promoting amount of one or more compounds selected from the group consisting of o-nitrophenol, p-nitrophenol and 5-nitroguaiacol, and salts thereof, in combination with at least one additives selected from the group consisting of vitamins, amino acids, inorganic salts or microelements.

3. The method of claim 1 wherein said animal is a fish.

4. The method of claim 1 wherein said animal is a mammal.

5. The method of claim 1 wherein said animal is poultry.

6. The method of claim 2 wherein said animal is a fish.

7. The method of claim 2 wherein said animal is a mammal.

8. The method of claim 2 wherein said animal is poultry.

9. The method of claim 1 wherein said one or more compounds are administered with a liquid or solid carrier.

10. The method of claim 2 wherein said one or more compounds are administered with a liquid or solid carrier.

11. The method of claim 1 wherein said one or more compounds are administered in an animal feed.

12. The method of claim 2 wherein said one or more compounds are administered in an animal feed.

13. The method of claim 1 wherein said one or more compounds are administered in water.

14. The method of claim 2 wherein said one or more compounds are administered in water.

* * * * *